(12) United States Patent
Knaub

(10) Patent No.: US 9,907,917 B2
(45) Date of Patent: Mar. 6, 2018

(54) CARPULE WARMER AND DISPENSER

(71) Applicant: Troy L. Knaub, Laramie, WY (US)

(72) Inventor: Troy L. Knaub, Laramie, WY (US)

(*) Notice: Subject to any disclaimer, the term of this patent is extended or adjusted under 35 U.S.C. 154(b) by 0 days.

(21) Appl. No.: 15/192,443

(22) Filed: Jun. 24, 2016

(65) Prior Publication Data

US 2016/0375201 A1  Dec. 29, 2016

Related U.S. Application Data

(60) Provisional application No. 62/183,986, filed on Jun. 24, 2015.

(51) Int. Cl.

| A61M 5/44 | (2006.01) |
|---|---|
| A61J 1/16 | (2006.01) |
| B65D 21/02 | (2006.01) |
| B65D 43/16 | (2006.01) |
| B65D 83/00 | (2006.01) |
| B65D 83/02 | (2006.01) |
| A61J 7/00 | (2006.01) |
| A61J 1/06 | (2006.01) |

(52) U.S. Cl.
CPC .............. *A61M 5/44* (2013.01); *A61J 1/16* (2013.01); *A61J 7/0084* (2013.01); *B65D 21/0201* (2013.01); *B65D 43/16* (2013.01); *B65D 83/0038* (2013.01); *B65D 83/02* (2013.01); *A61J 1/06* (2013.01); *A61J 2200/42* (2013.01)

(58) Field of Classification Search
None
See application file for complete search history.

(56) References Cited

U.S. PATENT DOCUMENTS

| 4,526,292 A * | 7/1985 | Waxman | A47F 1/10 221/131 |
|---|---|---|---|
| 4,718,573 A * | 1/1988 | Wenkman | A47G 21/12 221/202 |
| 5,482,183 A * | 1/1996 | Beal | A61J 7/0076 221/150 A |
| 5,860,563 A * | 1/1999 | Guerra | B65G 47/24 221/172 |
| 6,076,699 A * | 6/2000 | Seager | A47G 19/22 215/396 |
| 6,364,158 B1 * | 4/2002 | Dimoulis | A47F 1/10 221/238 |
| 8,757,433 B2 * | 6/2014 | Machers | G07F 11/20 211/59.2 |

OTHER PUBLICATIONS

International Search Report for PCT Patent Application No. PCT/US2016/039345 dated Feb. 3, 2017, 23 total pages.

* cited by examiner

*Primary Examiner* — Timothy R Waggoner
(74) *Attorney, Agent, or Firm* — Samuel M. Freund; Cochran Freund & Young LLC

(57) ABSTRACT

An apparatus for storing, warming and manually individually dispensing elongated cylindrical vials having different contents, while minimizing error and clutter, is described. Vials are stored in bins, which have manually operated dispensing members. Each bin may be separately heated using small incandescent bulbs or other heating elements. Adjustable temperature sensors may be placed in each bin to permit separate temperature control, and provide a high-temperature cutoff. One embodiment of the apparatus may be wall mounted to relieve congestion on horizontal surfaces. Another embodiment is suitable for table use, and has a reduced profile for clutter reduction.

9 Claims, 11 Drawing Sheets

CARPULE WARMER AND DISPENSER

CROSS-REFERENCE TO RELATED APPLICATIONS

The present application claims the benefit of U.S. Provisional Patent Application No. 62/183,986 for "Carpule Warmer And Dispenser", which was filed on Jun. 24, 2015, the entire content of which application is hereby specifically incorporated by reference herein for all that it discloses and teaches.

FIELD OF THE INVENTION

The present invention relates generally to vial or ampule warmers and dispensers and, more particularly, to cartridge warmers and dispensers that permit ampules having different contents to be separately and independently stored, warmed and dispensed.

BACKGROUND

Vial or ampule devices for storing, warming and dispensing small vials of medicine are commonly found in the offices of dentists, doctors and veterinarians. Maintaining vials of local anesthetics, such as novocaine, at a temperature close to body temperature is more comfortable to patients and animals for injection, and avoids trauma from thermal shock. Typically, dispensers are located on horizontal surfaces in treatment rooms.

SUMMARY OF THE INVENTION

Embodiments of the present invention overcome the disadvantages and limitations of the prior art by providing an apparatus for separately and independently storing and manually dispensing vials having different contents.

Another object of embodiments of the invention is to provide an apparatus for warming and separately and independently storing and manually dispensing vials having different contents.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for storing, warming and manually individually dispensing elongated cylindrical vials having different contents, hereof includes: at least one bin comprising: two vertical spaced-apart parallel side walls having a spacing suitable for permitting the vials to be horizontally disposed therebetween; a vertical front wall having an opening in a lower portion thereof, and an inner surface; a vertical guide member protruding into the at least one bin from the lower portion of the inner surface of the front wall, and extending into the opening thereof; a vertical rear wall; and a ramp attached to a lower portion of the rear wall and directed into the at least one bin, wherein the ramp has an outside and a bin side, and has holes therein for permitting heat to pass therethrough, wherein the two vertical side walls, the vertical front wall, the vertical rear wall, and the ramp form a bin volume, and wherein the ramp and the vertical guide member form a channel having an inlet facing the bin volume and an outlet facing the opening in the front wall, and through which the vials slide or roll due to gravity; a manually pivotable vial dispensing tray having an inner portion and an outer portion and disposed in the opening of the front wall of the at least one bin, the dispensing tray comprising: a vial blocking inner portion for reversibly blocking movement of the vials out of the channel; a bent section pivotably attached to the side walls, the bent section having a flanking member on opposing sides thereof for guiding the vials along the bent section, the bend in the bent section disposed in the region of the pivotable attachment; and a cup portion for holding one of the vials; a top for covering the at least one bin; at least one heating element disposed on the outside of the ramp for maintaining the at least one bin at a chosen temperature; and an electrical power source for providing power to the heating element.

In another aspect of the present invention and in accordance with its objects and purposes, the apparatus for storing, warming and manually individually dispensing elongated cylindrical vials having different contents, hereof includes: at least one bin comprising: two vertical spaced-apart parallel side walls having a spacing suitable for permitting said vials to be horizontally disposed therebetween; a vertical front wall having an opening in a lower portion thereof, and an inner surface; a vertical rear wall; a first ramp on which the vials slide or roll due to gravity, having one end thereof attached to the front wall in a lower portion thereof and above the opening thereof, and a second free end, the first ramp being directed into the at least one bin at a downward angle from said front wall to said rear wall, and having a length such that there is an opening with a chosen distance between the free end of the first ramp and said rear wall, wherein the first ramp has holes therein for permitting heat to pass therethrough, and wherein said two vertical side walls, the vertical front wall, the vertical rear wall, and the first ramp form a bin volume; a second ramp on which the vials slide or roll due to gravity and disposed below the first ramp, having one end thereof attached to the rear wall in a lower portion thereof, the second ramp being directed into the at least one bin at a downward angle from said rear wall to said front wall, and having a length such that the second ramp exits the first wall through the opening therein terminating in an upturned portion for retaining a vial; a manually operated vial dispensing actuator disposed in the vicinity of the rear wall and adapted to move in the vertical direction, the actuator capturing a single vial on the first ramp when disposed in a first position, and releasing the captured vial onto the second ramp through the opening when disposed in a second position, below the first position; wherein, the captured vial exits the at least one bin through the opening in the front wall and is retained in the upturned portion of the second ramp when the actuator is disposed in the second position; a top for covering the at least one bin; at least one heating element disposed below the first ramp and above the second ramp for maintaining the at least one bin at a chosen temperature; and an electrical power source for providing power to the at least one heating element.

Benefits and advantages of embodiments of the present invention include, but are not limited to, providing an apparatus for storing, warming and manually individually dispensing elongated cylindrical vials having chosen contents, such that vials containing the chosen contents can be heated and maintained at selected temperatures, and the likelihood of confusing vials having chosen contents is minimized.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 4A is a schematic representation of a perspective front view of the embodiment of the wall or table mounted apparatus for storing, warming and dispensing ampules shown in FIG. 1 hereof, further illustrating a divided bin for storing needles and swabs which may be formed integrally with or attached to either side of the apparatus, or to both sides thereof, while

DETAILED DESCRIPTION

Briefly, the present invention includes apparatus for storing, warming and manually individually dispensing elongated cylindrical vials having different contents, while minimizing error and clutter. Vials are stored in bins, which have manually operated dispensing members. Clearly, any number of bins may be utilized. Each bin may be separately heated using small incandescent bulbs, as an example. Clearly, other heating sources may be employed, such as resistive etched foil heaters and wire heaters, and the like. Adjustable temperature sensors may be placed in each bin to permit separate temperature control and provide a high-temperature cutoff. One embodiment of the invention may be wall mounted to relieve congestion on horizontal surfaces. In this situation, battery power might be utilized to reduce clutter from power cords. Another embodiment is suitable for table use, and has a reduced profile for clutter reduction.

In what follows, the terms vial, ampule, ampoule, carpule, and cartridge are used interchangeably.

Figure 1:
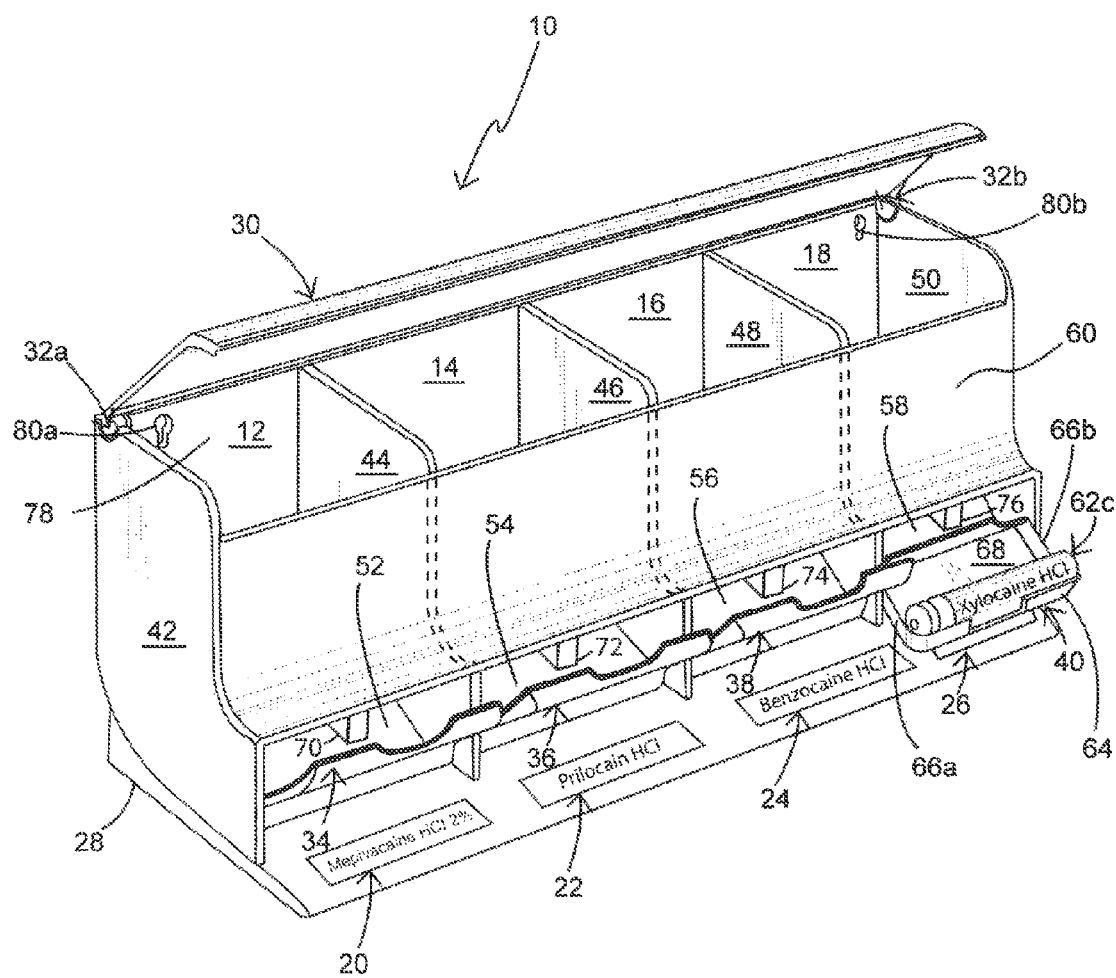
FIG. 1 is a schematic representation of a perspective front view of a wall or table mounted apparatus for storing, warming and dispensing four kinds of ampules.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1, a schematic representation of a perspective front view of an embodiment of wall or table mounted apparatus, 10, for storing, warming and dispensing four kinds of ampules from adjacent bins. Bins 12, 14, 16, and 18, are adapted to hold commercially available ampules, containing an injectable local anesthetic for dental use, as an example. Shown are labels, 20, 22, 24, and 26, for Mepivacaine HCl, Prilocaine HCL, Benzocaine HCl, and Xylocaine HCl, respectively, mounted on base, 28, again as examples. Some or all of the bins may contain the ampules having the same contents, if desired. Front opening lid, 30, is shown hinged, 32a, and 32b, in the rear of the apparatus, for loading the bins and for insulation of the heated ampules, but may be similarly hinged in the front for a back opening option. Lid 30 is illustrated as a single unit covering bins 12-18, but, if desired, each bin may have its own covering lid. Lid 30 may also be held on the top of bins 12-18 by gravity, but otherwise unconnected to the bins. Clearly, many lid mounting arrangements are possible.

Each bin has a manually operated ampule dispensing tray, 34, 36, 38, and 40, respectively, pivotably mounted on side walls, 42, 44, 46, 48, and 50, and disposed in openings, 52, 54, 56, and 58, respectively, of curved front wall, 60, of apparatus 10, for dispensing individual ampules as needed. Elongated, cylindrical vial, 62c, is shown resting in cupped outer portion, 64, of tray 40 of bin 18, having been guided there by flanking members, 66a and 66b formed on the sides of pivoting member, 68. Bins 12, 14, and 16 may have similar structure to bin 18. Vial 62c, having been warmed and selected, is ready to be removed by the user thereof. As will be discussed in more detail hereinbelow, guide members, 70, 72, 74, and 76, direct the motion of vials in bins 12, 14, 16, and 18, respectively, toward openings 52, 54, 56, and 58, respectively.

Back wall, 78, of apparatus 10 has holes, 80a, and 80b, adapted for receiving screws or other fastening devices for wall mounting of apparatus 10. Alternatively, apparatus 10 may rest on base 28 on a table or other horizontal surface.

Figure 2:
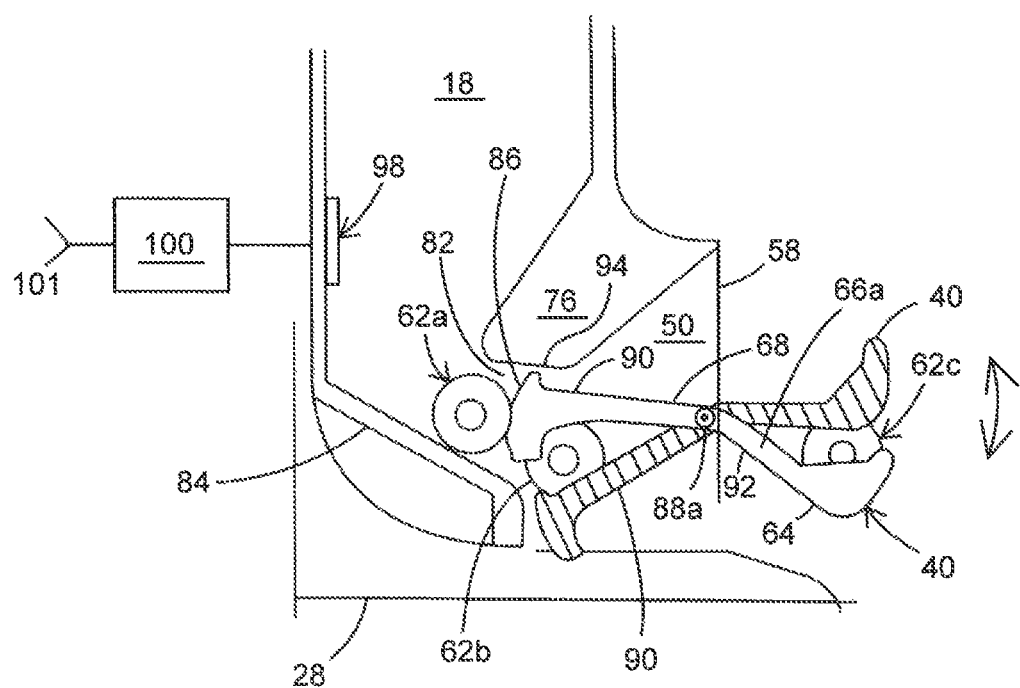
FIG. 2 is a schematic representation of a sectional side view of the apparatus shown in FIG. 1, hereof, illustrating a manual dispensing tray and a temperature sensor.

FIG. 2 is a schematic representation of a sectional side view of the apparatus shown in FIG. 1, hereof, illustrating manual dispensing tray 40 in its open position offering vial 62c for removal and use. As may be seen from FIG. 1, hereof, dispensing tray 40 is disposed in front opening 58 of wall 60, and permits vials, 62a, and 62b, as well as those behind them in bin 18 (not shown in FIG. 2) to be accessed. Vials loaded into bin 18 are gravity fed into channel, 82, bounded by ramp, 84, formed in the lower portion of back wall 72, and guide member 76, until the vials come into contact with enlarged inner portion, 86, of dispensing tray 40, which is effective for stopping vials when in its dispensing mode as will be discussed in more detail hereinbelow. The thickness of guide member 76 is chosen such that the vials do not rotate about a radial axis and block channel 82.

Pivoting member 68 of tray 40 is adapted to pivot about pivot locations, 88, at opposing positions on the side of the tray. This may be accomplished in several ways, one example of which is employing pivot pins attached to walls 48 and 50 at locations matching opposing locations 88a in tray 40 (location 88b and pins not shown in FIG. 2), which are directed into bin 18 and which are received by holes in tray 40 or a slot therein, thereby permitting tray 40 to pivot. Pivoting member 68 of tray 40 is bent in the region of pivot locations 88, forming two generally flat sections: back section 90, which terminates in enlarged portion 86, and outer portion 92, which terminates in cupped portion 64.

Apparatus 10 may be constructed of heat-resistant, sturdy, sterilizable plastics such as Polysulfone, Polyethersulfone, and Polyphenylsulfone, such that front wall 60 may transparent.

In operation, tray 40 is disposed such that enlarged inner portion 86 blocks movement of vials into channel 82. If a vial is desired, cup portion 64 of tray 40 is pivoted upward to the position shown by the hatched view of tray 40, after which a vial can roll or slide onto back section 90 of the hatched view of tray 40. Shown in FIG. 2 is vial 62a, initially blocked by enlarged portion, 86, rolling or sliding onto pivoting member 68, and consequently labeled vial 62b. Cup portion 64 is next pivoted downward such that vial 62b slides or rolls down pivoting member 68 onto front section 92 and into outer cup portion 64, and consequently labeled vial 62c, where it is held for removal by a user of apparatus 10. Hook, 94 may be formed in the upper surface of enlarged portion 86 to assist vial 62b in moving toward the front end of tray 40.

Also shown in FIG. 2 is temperature sensor, 98, and temperature reader, 100, for measuring and reporting the temperature of bin 18. Similar sensors and readers may be employed in bins, 12, 14, and 16, or reader 100 may be used to measure and process input from temperature sensors in each bin. Reader 100 is powered by electrical source, 101, which may include ac or dc available from electrical power lines directed to electrical receptacles in buildings around the world, and battery power.

Figure 3:
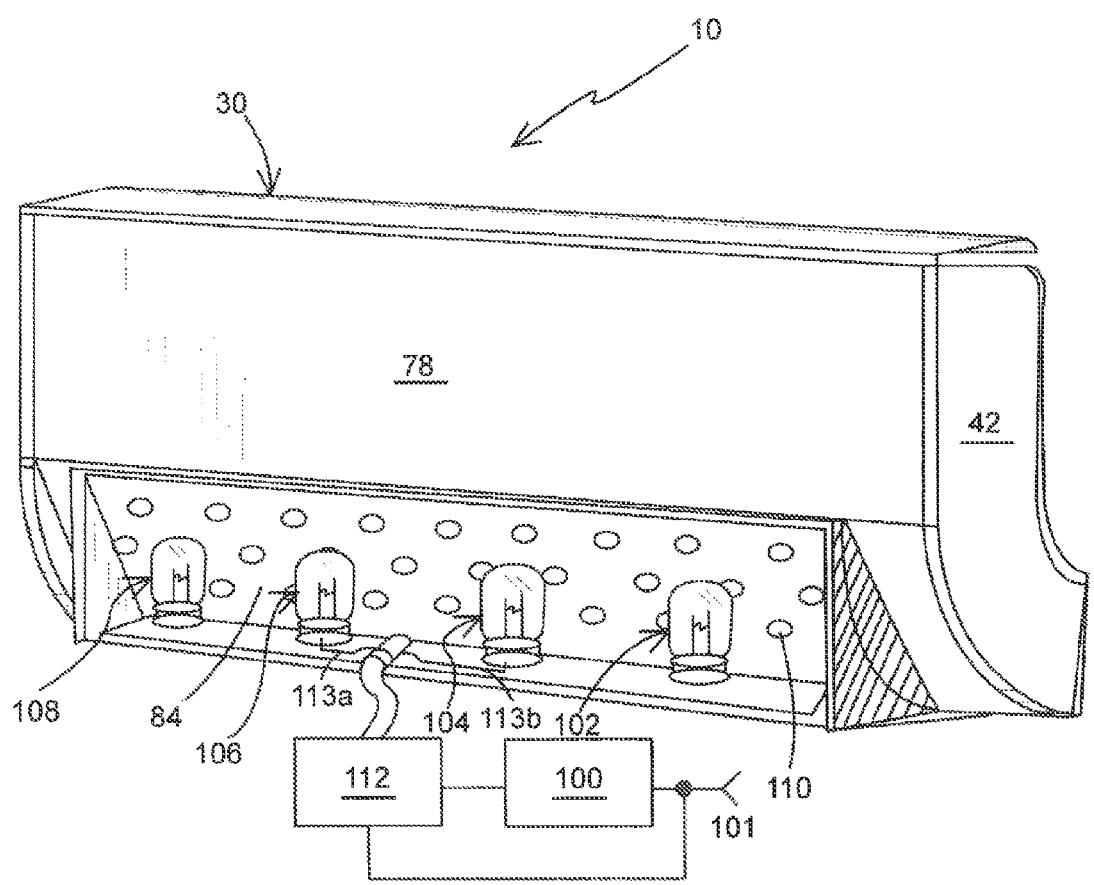
FIG. 3 is a schematic representation of a perspective rear view of the apparatus shown in FIG. 1, hereof, illustrating incandescent bulbs for providing heat to the ampules.

FIG. 3 is a schematic representation of a rear perspective view of the apparatus shown in FIG. 1, hereof, illustrating incandescent bulbs, 102, 104, 106, and 108, for providing heat to the ampules or vials in bins 12, 14, 16, and 18, respectively, through holes, 110, in ramp 84. Incandescent bulbs, shown as the heating source, may be individually controlled using controller, 112, which receives individual bin temperature information from temperature reader 100, and controls the current in each bulb or other source of heat. This permits each bin to be separately temperature controlled, if desired. Controller 112 is also shown being powered by ac, dc, or battery electrical source 101. A simpler version of temperature reader 100 and controller 112 might discontinue heating if the temperature rises above a common preset temperature for all of the bins. As stated above, other well-known electrical heating sources may be employed.

Figure 4A:
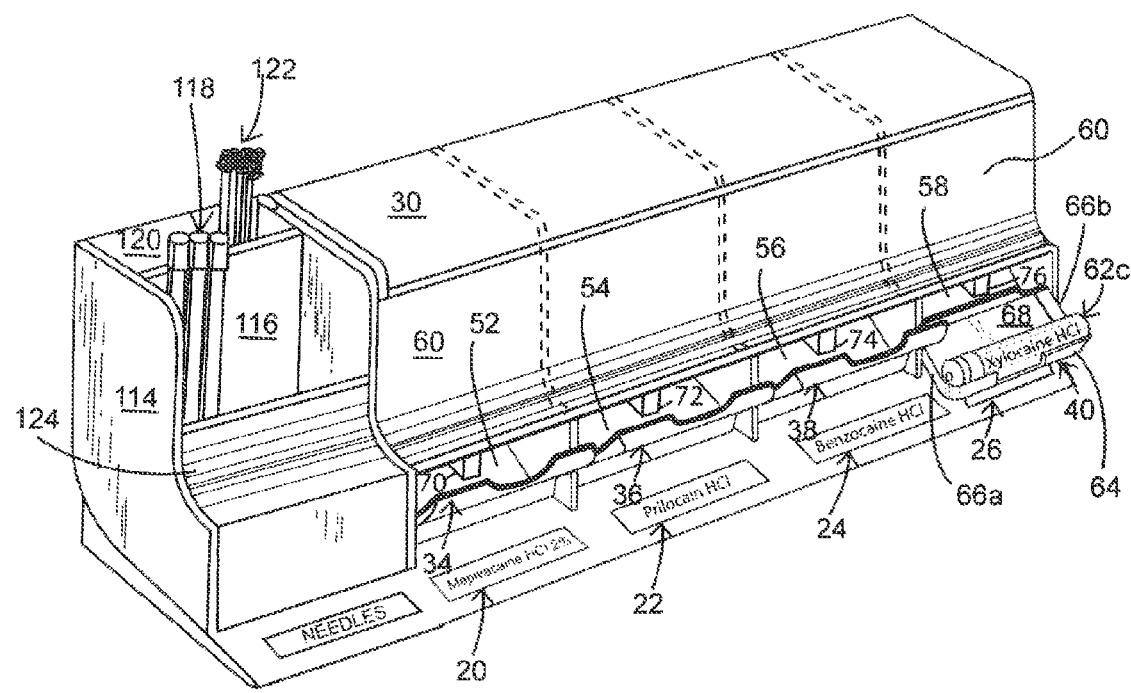

FIG. 4A is a schematic representation of a perspective front view of another embodiment of wall or table mounted apparatus 10 showing divided container, 114, having a first compartment or bin, 116, for vertically storing needles in plastic cases, 118, and a second compartment or bin, 120, for vertically storing swabs, 122. Container 114 may be formed integrally with or attached to either side of apparatus 10, or to both sides thereof. Since wall 60 of apparatus 10 is curved, wall 124 of container 114 may be curved for purposes of form or style. To prevent plastic cases 118 from being difficult to recover if they fall sideways in bin 116, a horizontal floor, not shown in FIG. 4A, may be formed therein such that the cases are readily retrieved.

Figure 4B:
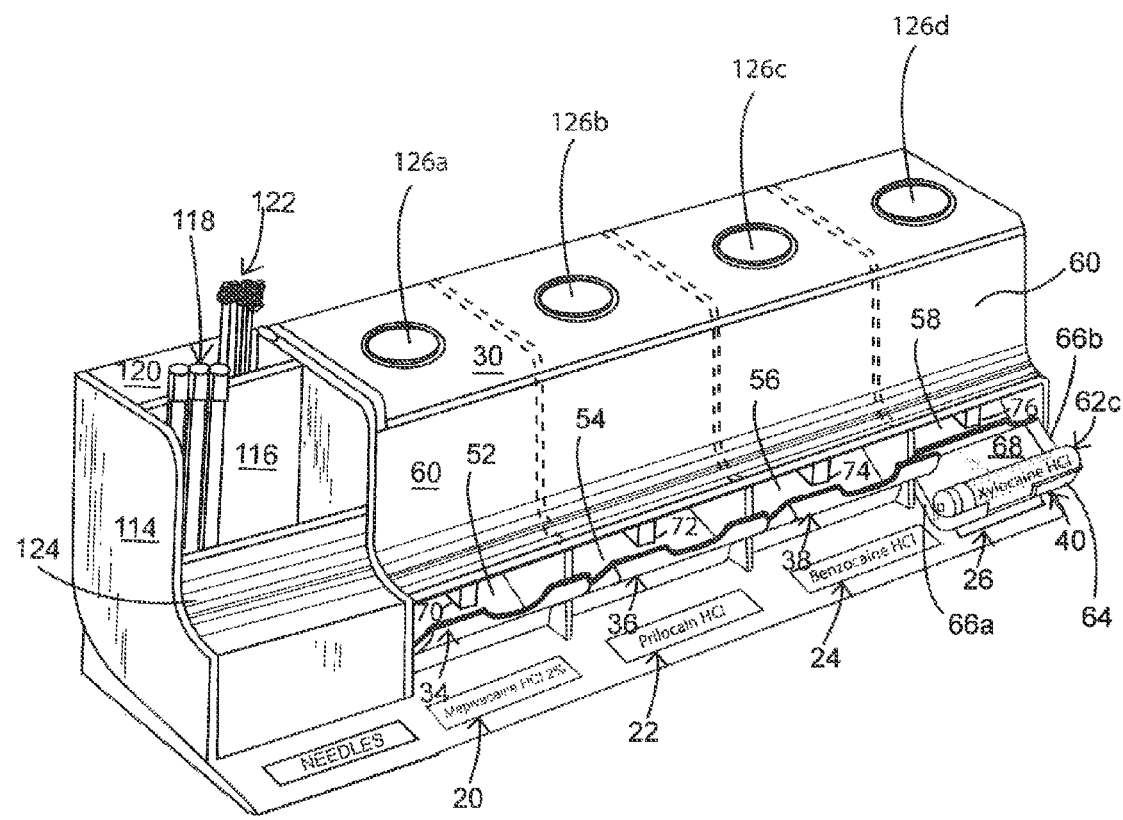
FIG. 4B is a schematic representation of a perspective front view of the embodiment of wall or table mounted apparatus illustrated in FIG. 4A showing molded, raised rings on hinged, front-opening lid for resting topical anesthetic carpules while in use.

FIG. 4B is a schematic representation of a perspective front view of the embodiment of wall or table mounted apparatus 10 showing molded, raised rings, 126a-126d, on hinged, front-opening lid, 30, for resting topical anesthetic carpules while in use.

Figure 5:
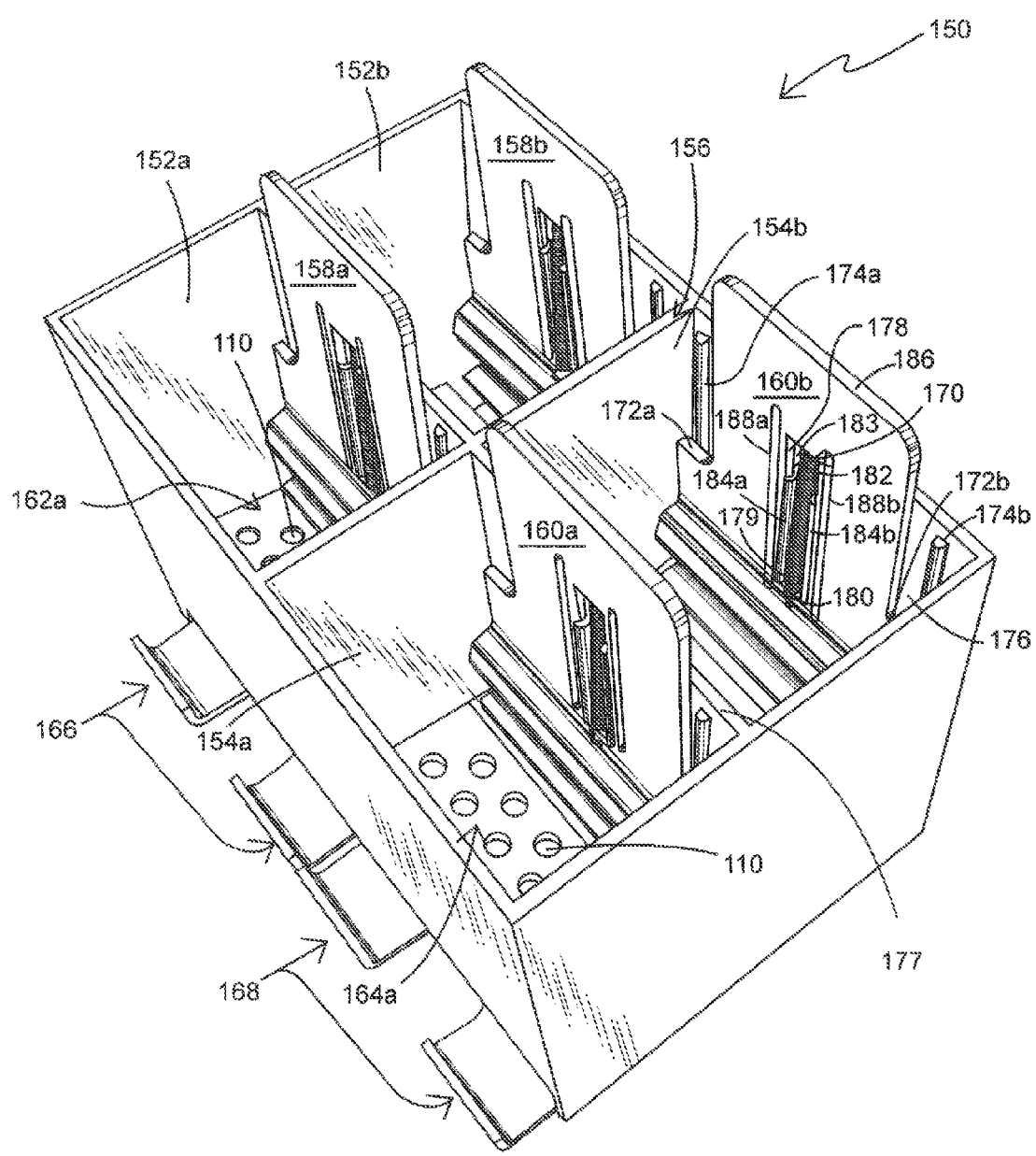
FIG. 5 is a schematic representation of a perspective top view of a tandem bin embodiment of a table mounted apparatus for storing, warming and dispensing four kinds of ampules from tandem and adjacent bins, showing vertical, spring-loaded, manual dispenser actuators, perforated, slanted bin floors, and dispensing trays.

FIG. 5 is a schematic representation of a perspective top view of a tandem bin embodiment of a table mounted apparatus, 150, for storing, warming and dispensing four kinds of ampules from tandem and adjacent bins. Tandem bins 152a,b, and 154a,b, are separated by wall, 156. Clearly, additional adjacent tandem bin sets can be employed, as can a greater numbers of tandem bins. Shown also are vertical, spring-loaded, manual dispenser actuators, 158a,b, and 160a,b, perforated (vent holes 110), slanted bin floors, 162a, and, 164a, for bins 152a and 154a, respectively, bin floors, 162b, and, 164b, for bins 152b and 154b, respectively, and dispensing trays, 166, and 168, shown having split exit segments, for receiving carpules from both bins 152a and 152b, and 154a and 154b, respectively.

Using bin 154b as an example, shown in FIG. 5 is spring, 170, for pulling actuator 160b upward such that the portions of flat actuator 160b below shoulders, 172a,b, ride against vertical protrusions, 174a,b, formed in rear wall, 176, of bin 154b, whereby actuator 160b is kept away from rear wall 176. Spring 170 is disposed in slot, 178, formed in actuator 160b, and attached at one end, 179, below lower end, 180, of slot 178, and at its other end, 182, to rear wall 176, not shown in FIG. 5, above upper end, 183, of slot 178. Curved, parallel vertical guides, 184a,b, on either side of spring 170, also formed in rear wall 176, and not shown in FIG. 5, capture actuator 160b on either side of slot 178, such that actuator 160b can be moved in a downward direction against spring 170 by a user pressing on top horizontal edge, 186, of actuator 160b. Actuator 160b automatically returns to its upward, rest position, under the action of spring 170 once pressure is released from top edge 186, when lower end 180 of slot 178 reaches vertical guides 184a,b. Vertical slots, 188a,b, formed parallel to slot 178 in actuator 160b, provide flexibility to actuator 160b in the region of slot 178, thereby permitting actuator 160b to be inserted into and captured by guides 184a,b. Clearly, there are other methods for guiding and directing actuator 160b into its upward, base or resting configuration.

Figure 6A:
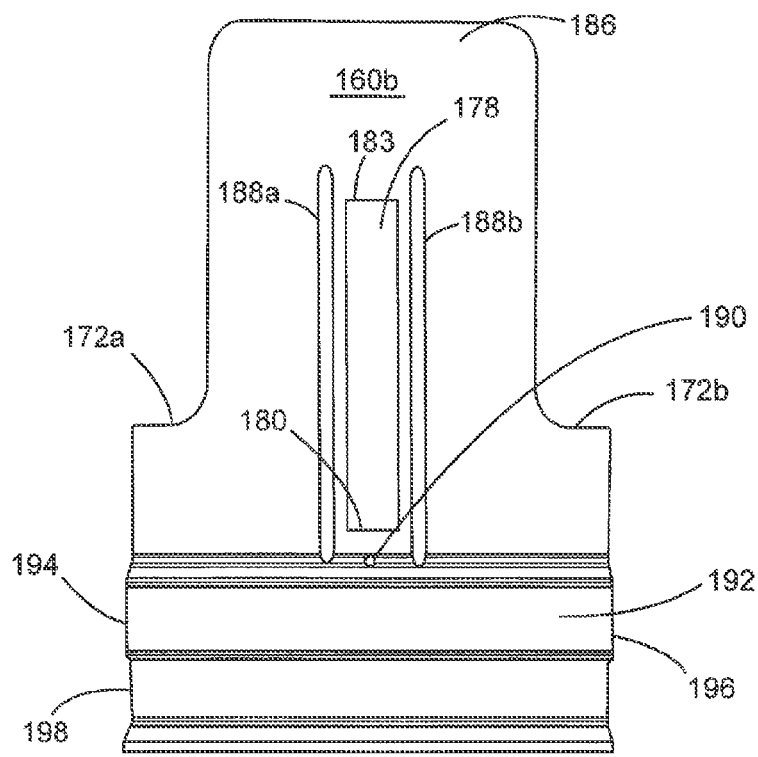
FIG. 6A is a schematic representation of the front view of an actuator illustrating a horizontally disposed convex cylindrical portion, and a horizontally disposed concave cylindrical portion, adjacent and parallel to and below the convex cylindrical portion.

FIG. 6A is a schematic representation of the front view of actuator 160b, illustrating lower spring 170 mounting hole, 190, in actuator 160b, horizontally disposed convex cylindrical portion, 192, which extends from side 194 of actuator 160b to opposing side 196 thereof, and horizontally disposed concave cylindrical portion, 198, which extends from side 194 of actuator 160b to opposing side 196 thereof, adjacent and parallel to and below cylindrical portion 192. The furthest extent of rear surface, 200, of cylindrical portion 198 is in the plane of rear surface 202 of actuator 160b.

Figure 6B:
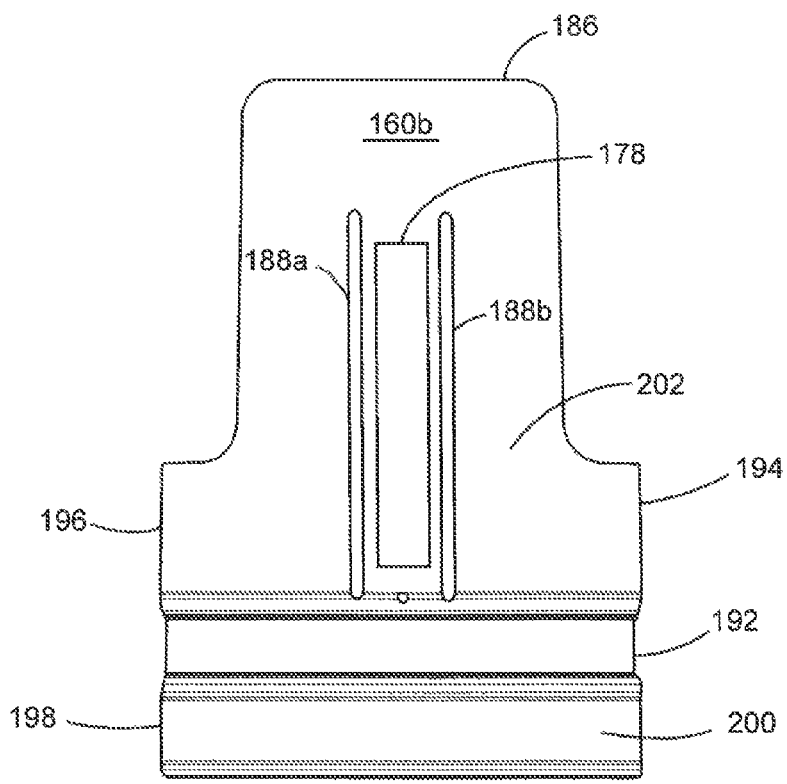
FIG. 6B is a schematic representation of the rear view of the actuator shown in FIG. 6A hereof.
Figure 6C:
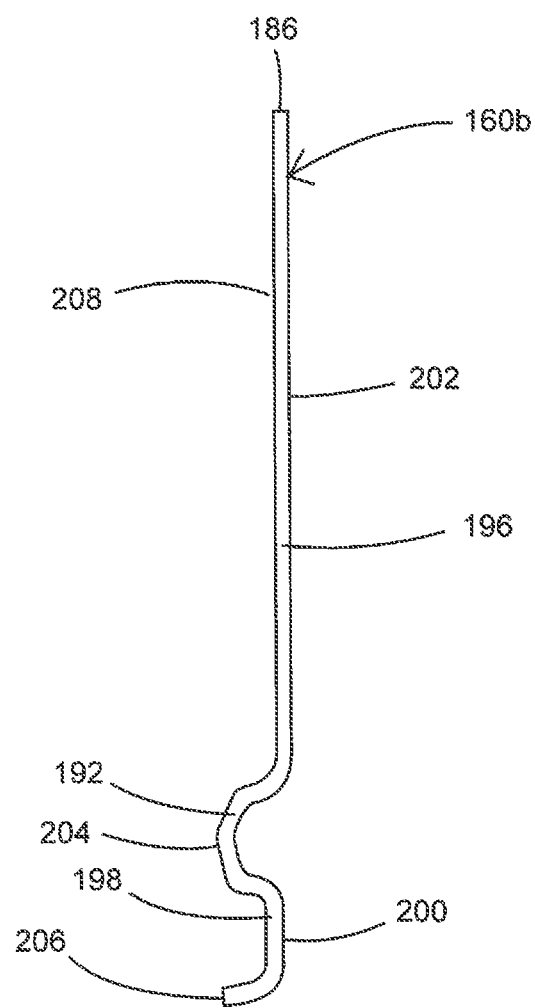
FIG. 6c is a schematic representation of a side view thereof.

FIG. 6B is a schematic representation of the rear view of actuator 160b, while FIG. 6c is a schematic representation of a side view thereof, showing that front surface, 204, of convex cylindrical portion 192 extends forward of the plane of front face, 206, and rear surface 200 is in the plane of rear face 202. Bottom end, 206, of concave cylindrical portion 198 extends approximately as far as forward as front surface 204 of convex cylindrical portion 192 from the plane of front face 208.

Figure 7:
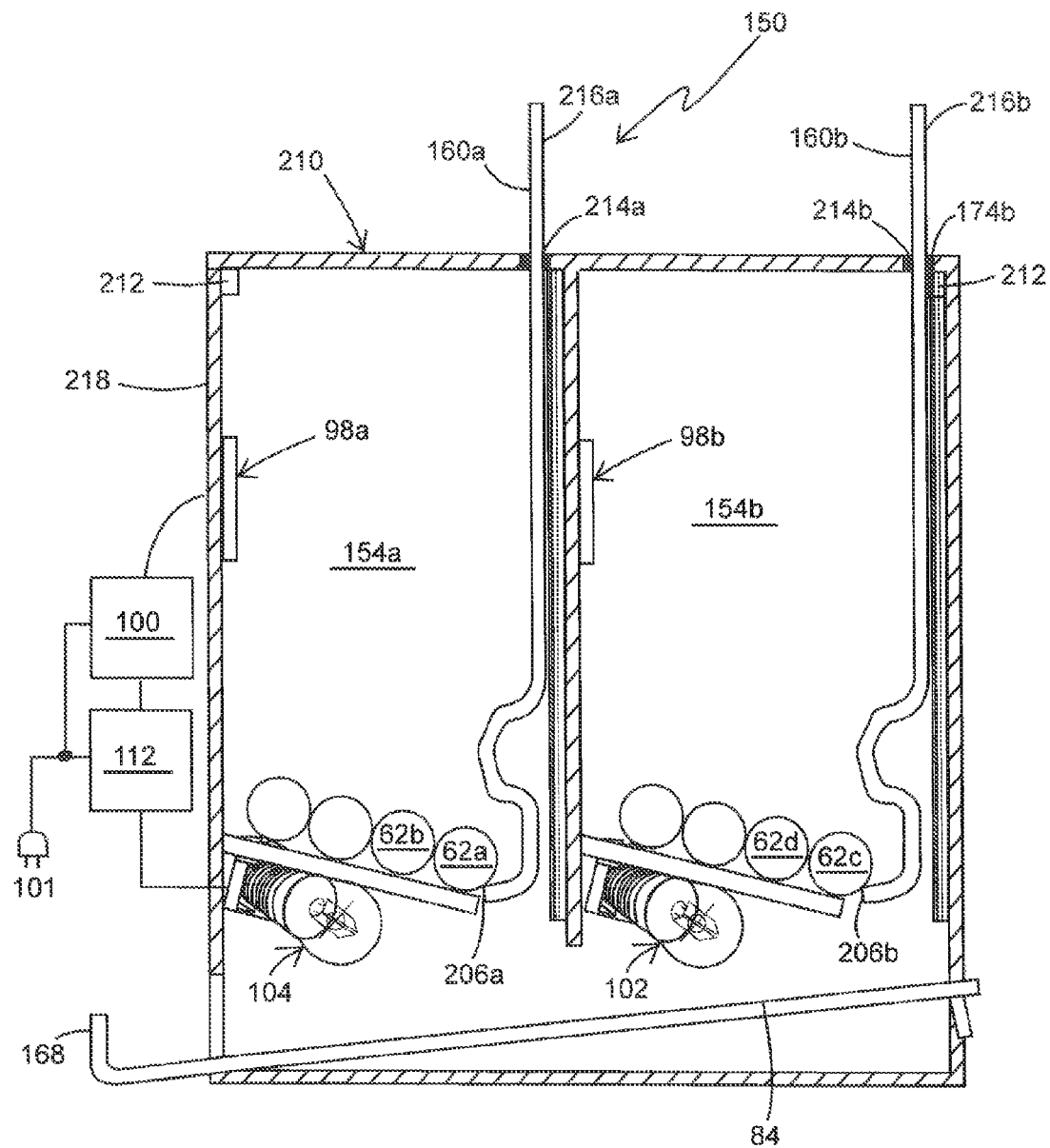
FIG. 7 is a schematic representation of a side cutaway view of carpule warmer/dispenser shown in FIG. 1 hereof, illustrating the actuators in their rest positions, and a removable cover having slots adapted for permitting the top portions, of the actuators to freely slide therethrough.

FIG. 7 is a schematic representation of a side cutaway view of carpule warmer/dispenser 150 shown in FIG. 1 hereof, illustrating actuators 160*a,b* in their rest positions. Removable cover, 210, is shown having lip, 212, for securing it onto the top of the bins, and slots, 214*a*, and, 214*b*, adapted for permitting the top portions, 216*a* and, 216*b*, of actuators 160*a,b*, respectively, to freely slide therethrough. The size of cover 210 will depend on the number of tandem and adjacent bins in dispenser 150. Removable cover 210 also provides thermal insulation to the bins. Shown also are carpules 62*a-d*, as illustrative of the carpules filling each of bins 160*a* and 160*b*. The carpules are prevented from moving by bottom ends 206*a* and 206*b* for actuator 160*a* and 160*b*, respectively, when these actuators are in their rest positions. In another embodiment, actuators 160*a,b* may have a resting position such that a carpule 62*a* or 62*b* moves into concave cylindrical portion 198 of actuator 160, and be selected, awaiting actuator 160 to be moved downward for their release.

Incandescent bulbs, 102, 104, or other electrical heating elements, provide heat to the ampules or vials in bins 154*a,b*, respectively, through holes, 110, in ramp 84. The incandescent bulbs may be individually controlled using controller, 112, which receives individual bin temperature information from temperature reader 100, read from temperature sensors 98*a* and 98*b*, and controls the current supplied to each bulb. This permits each bin to be separately temperature controlled, if desired. A simpler version of temperature reader 100 and controller 112 might discontinue heating if the temperature rises above a common preset temperature for all of the bins. Ramp 84 permits vials from either of tandem bins 160*a* or *b* to reach dispenser tray 168. It should be mentioned that in the event that only a single bin is used, ramp 84 would be attached to rear wall, 177, of the single bin.

Apparatus 150 may be constructed of heat-resistant, sturdy, sterilizable plastics such as Polysulfone, Polyethersulfone, and Polyphenylsulfone, such that front wall, 218, may transparent.

Figure 8A:
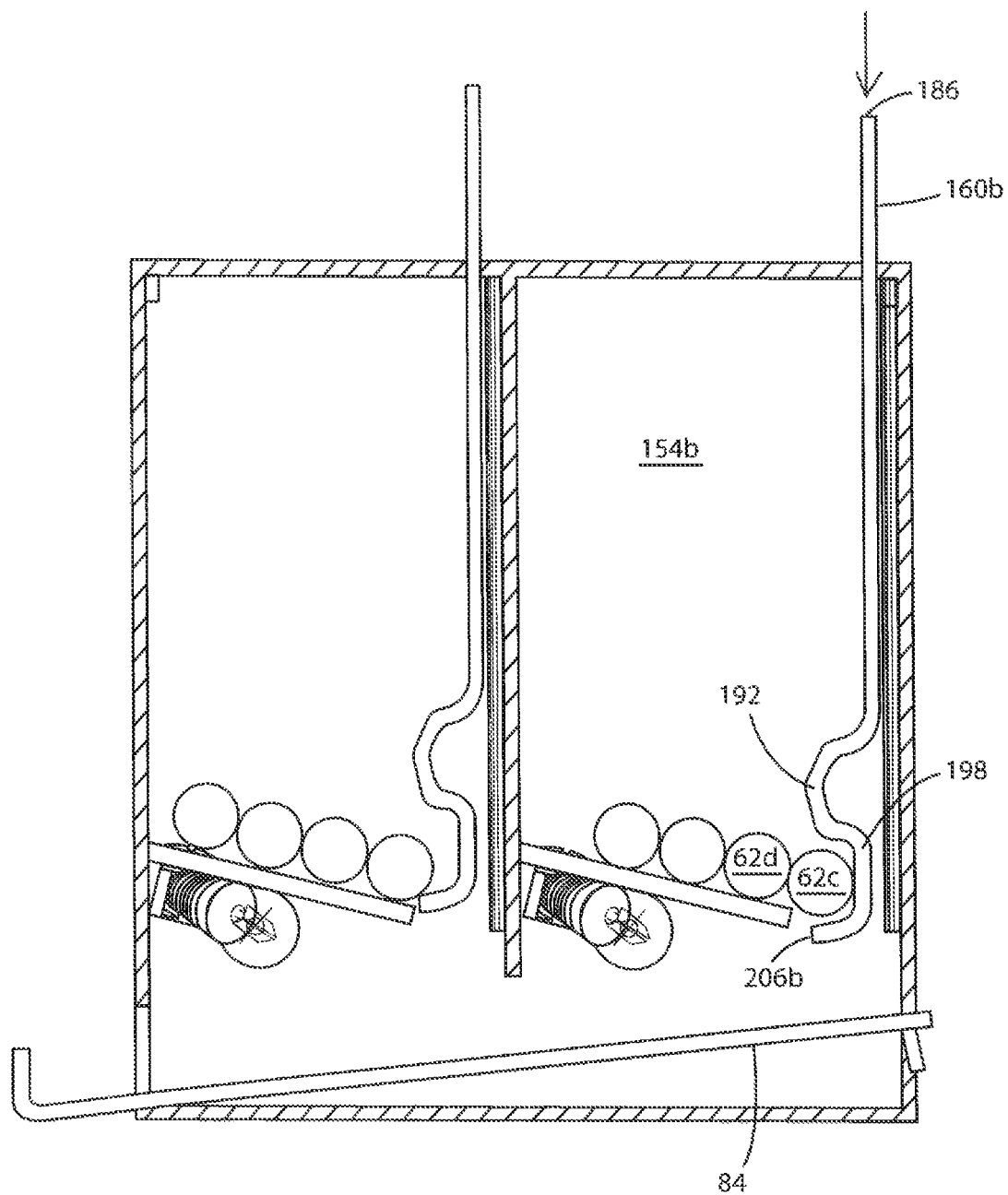
FIGS. 8A and 8B illustrate warmer/dispenser in use dispensing vials.
Figure 8B:
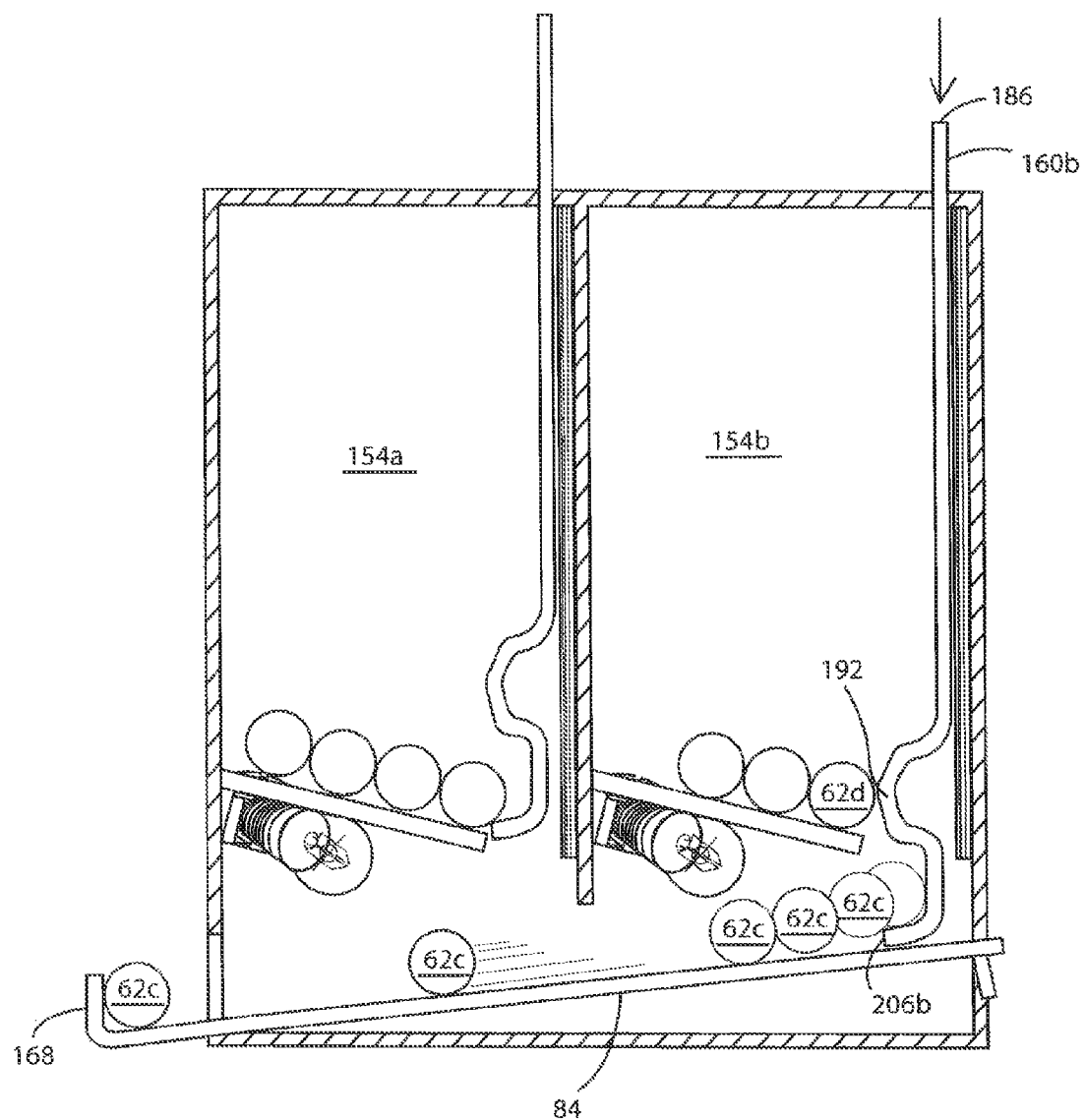

FIGS. 8A and 8B illustrate warmer/dispenser 150 in use. To remove vial 62*c* from bin 154*b*, as an example, a user depresses actuator 160*b* such that concave cylindrical portion 198 is moved in a downward direction such that vial 62*c*, previously held by bottom end 206*b*, rolls into it, as seen in FIG. 8A. As actuator 160*b* is further depressed, concave cylindrical portion 198 moves further downward until bottom end 206*b* is stopped by ramp 84, and vial 62*c* is free to roll down ramp 84, and into dispensing tray 168 for removal by the user, while vial 62*d* is blocked from rolling forward by convex cylindrical portion 192. Upon release of actuator 160*b*, spring 170 pulls actuator 160*b* upward to its rest position, whereby vial 62*d* is blocked from rolling forward by bottom end 206*b*.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for storing, warming and manually individually dispensing elongated cylindrical vials having different contents, comprising:
   at least one bin comprising:
      two vertical spaced-apart parallel side walls having a spacing suitable for permitting said vials to be horizontally disposed therebetween;
      a vertical front wall having an opening in a lower portion thereof, and an inner surface;
      a vertical guide member protruding into said at least one bin from the lower portion of the inner surface of said front wall, and extending into the opening thereof;
      a vertical rear wall; and
      a ramp attached to a lower portion of said rear wall and directed into said at least one bin, wherein the ramp has an outside and a bin side, and has holes therein for permitting heat to pass therethrough, wherein said two vertical side walls, said vertical front wall, said vertical rear wall, and said ramp form a bin volume, and wherein said ramp and said vertical guide member form a channel having an inlet facing the bin volume and an outlet facing the opening in said front wall, and through which said vials slide or roll due to gravity;
      a manually pivotable vial dispensing tray having an inner portion and an outer portion and disposed in the opening of said front wall of said at least one bin, said dispensing tray comprising:
         a vial blocking inner portion for reversibly blocking movement of said vials out of the channel;
         a bent section pivotably attached to each of said side walls, the bent section having a flanking member on opposing sides thereof for guiding said vials along the bent section, the bend in the bent section disposed in the region of the pivotable attachment; and
         a cup portion for holding one of said vials;
      a top for covering said at least one bin;
      a heating element disposed on the outside of said ramp; and
      an electrical power source for providing power to said heating element.

2. The apparatus of claim 1, wherein said heating element comprises a resistive heater.

3. The apparatus of claim 1, wherein said heating element comprises an incandescent light bulb.

4. The apparatus of claim 1, wherein said front wall of said bin comprises clear plastic.

5. The apparatus of claim 1, further comprising a temperature sensor and a high-temperature cut-off, for controlling said power source.

6. The apparatus of claim 1, wherein said electrical power source comprises at least one battery.

7. The apparatus of claim 1, wherein said top is hingedly attached to said vertical rear wall.

8. The apparatus of claim 7, further comprising at least one raised ring disposed on said hinged top for resting said carpules.

9. The apparatus of claim 1, further comprising an external container attached to or integrally formed with said at least one bin.

* * * * *